United States Patent [19]

Cainelli et al.

[11] Patent Number: 4,732,897

[45] Date of Patent: Mar. 22, 1988

[54] STEROIDIC 5α-REDUCTASE INHIBITORS

[75] Inventors: Gianfranco Cainelli, Bologna; Giorgio Martelli, S. Lazzaro di Savena; Mauro Panunzio, Bologna; Giuseppe Spunta, Ozzano dell'Emilia; Giuliano Nannini, Bresso; Enrico di Salle, Milan, all of Italy

[73] Assignees: Farmitalia Carlo Erba, S.p.A., Milan; Consiglio Nazionale Delle Ricerche, Rome, both of Italy

[21] Appl. No.: 825,348

[22] Filed: Feb. 3, 1986

[30] Foreign Application Priority Data

Mar. 7, 1985 [GB] United Kingdom ............... 8505862

[51] Int. Cl.$^4$ .................. C07J 73/00; A61K 31/58
[52] U.S. Cl. .................... 514/222; 514/234; 514/236; 514/253; 514/284; 260/397.1; 544/60; 544/125; 544/361; 546/77; 546/78
[58] Field of Search ............... 546/77, 78; 514/284, 514/222, 234, 236, 253; 544/60, 125, 361

[56] References Cited

U.S. PATENT DOCUMENTS 4,220,775  9/1980  Rasmusson et al. ................ 546/77
4,377,584  3/1983  Rasmusson et al. ............. 546/77 X
4,388,241  6/1983  Monks ........................... 260/397.1

FOREIGN PATENT DOCUMENTS 1042291  11/1961  United Kingdom .

OTHER PUBLICATIONS

Doorenbos et al., Chemical Abstracts, vol. 63; 10017c–e (1965).
Varricchio, Chemical Abstracts, vol. 66:44027f (1967).
Shoppee et al., J. Chem. Soc. (1962), pp. 2275–2285.
Djerassi, "Steroid Reactions, an Outline for Organic Chemists", Holden-Day, Inc., San Francisco (1963), pp. 513–518.
Rasmusson G. H. et al., "Azasteroids as Inhibitors of Rat Prostatic 5-Reductase" J. Med. Chem. 1984, 27, 1690–1701.
Farmdoc Abstract 794038/44, Merck & Co., Inc. EP 4949, 1979.

Primary Examiner—Donald G. Daus
Assistant Examiner—Diana G. Rivers
Attorney, Agent, or Firm—Murray and Whisenhunt

[57] ABSTRACT

The present invention relates to new 4-aza-17β-substituted 5α-androstan-3-ones, to a process for their preparation, to pharmacological compostions containing them, and to the use of said compounds as inhibitors of androgen action by means of testosterone 5-reductase inhibition.

9 Claims, No Drawings

STEROIDIC 5α-REDUCTASE INHIBITORS

The present invention relates to new 4-aza-17β-substituted 5α-androstan-3-ones, to a process for their preparation, to pharmaceutical compositions containing them, and to the use of said compounds as inhibitors of androgen action by means of testosterone 5α-reductase inhibition. In the androgen responsive tissues the action of testosterone is mediated primarily through its 5α-reduced metabolite, dihydrotestosterone (DHT) (Bruchowsky N., Wilson J. D.; J. Biol. Chem. 243, 5953, 1968). The conversion of testosterone to dihydrotestosterone is catalyzed by the enzyme 5α-reductase and if 5α-reductase is inhibited, the formation of dihydrotestosterone is reduced and its specific androgenic effect is attenuated or prevented.

5α-reductase inhibitors may find medical application for the treatment of hyperandrogenic conditions, i.e. certain prostatic diseases, such as benign prostatic hypertrophy and prostatic cancer, and certain skin-hair conditions, such as acne, seborrhoea, female hyrsutism and male pattern baldness (Siiteri P. K., Wilson J. D., J. Clin. Invest. 49, 1737, 1970; Price V. H., Arch. Dermatol. III, 1496, 1975; Sandberg, A.A., Urology 17, 34, 1981). Also breast cancer treatment can take advantage from use of 5α-reductase inhibitors as the said tumor is known to be aggravated by presence of androgens. We have found a new group of 4-aza-steroid derivatives with testosterone 5α-reductase-inhibiting properties. Accordingly the present invention provides novel 4-aza-17β-substituted androstan-3-one derivatives of the following formula (I)

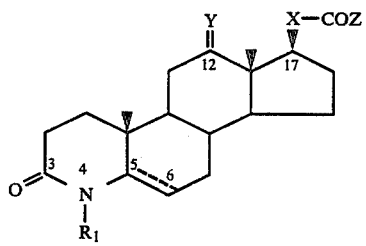

wherein
R$_1$ is
(a) hydrogen;
(b) C$_1$-C$_6$ alkyl unsubstituted or substituted by a substituent chosen from carboxy, halogen and amino;
(c) a C$_6$-C$_{10}$ aryl or C$_7$-C$_{10}$ aralkyl group, either unsubstituted or ring substituted by one or more substituents chosen from C$_1$-C$_6$ alkyl, halogen, nitro, amino and hydroxy, or
(d) —OR$_2$ wherein R$_2$ either has one of the meanings (a), (b) and (c) reported above for R$_1$; or is a C$_2$-C$_{22}$-carboxylic acyl or a hydroxy protecting group;
X is direct bond or a straight or branched C$_1$-C$_6$ aliphatic hydrocarbon chain;
the symbol =Y represents

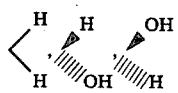

or =O;
Z is
(a') hydroxy;
(b') C$_1$-C$_6$ alkoxy; or
(c')

wherein each of R$_3$ and R$_4$ is, independently, hydrogen or C$_1$-C$_6$ alkyl; or R$_3$ and R$_4$, taken together with the nitrogen atom to which they are linked, form a pentatomic or hexatomic heteromonocyclic ring optionally containing an additional heteroatom chosen from N, O and S; and
the symbol  represents a single or a double bond, provided that the symbol =Y does not represent $$\diagup^H_{\diagdown H}$$

when R$_1$ has one of the meanings (a), (b) and (c) reported above.

The invention includes also the pharmaceutically acceptable salts of the compounds of formula (I) as well as all the possible isomers of formula (I) and their mixtures.

In this specification the alkyl groups, including the aliphatic moieties of the aralkyl and alkoxy groups, may be branched or straight chain.

A C$_1$-C$_6$ alkyl group is, preferably, C$_1$-C$_4$ alkyl, in particular methyl or ethyl; a C$_6$-C$_{10}$ aryl group is, preferably, phenyl, α-naphthyl or β-naphthyl, most preferably phenyl. A C$_7$-C$_{10}$ aralkyl group is, preferably, benzyl.

A halogen atom is, preferably, chlorine or bromine.

A C$_2$-C$_{22}$ carboxylic acyl may be an acyl group derived either from an optionally halosubstituted aliphatic carboxylic acid such as, e.g., acetic or propionic, or halo-acetic, e.g., chloro- or bromo-acetic, acid, or a fatty carboxylic acid such as, e.g., heptanoic, octanoic, dodecanoic, myristic, palmitic or stearic acid; or from an aromatic carboxylic acid such as, e.g., benzoic acid optionally substituted by C$_1$-C$_6$ alkyl, e.g. methyl, halogen, e.g. chlorine or bromine, nitro, amino or hydroxy.

A hydroxy protecting group may be any group, preferably an ether group, convertible to hydroxy under mild reaction conditions, e.g. acid hydrolysis. Examples are acetalic ether, enol ether and silyl ether residues, preferred groups being dimethyl tert.butyl silyl, trimethylsilyl and 2-tetrahydropyranyl, most preferably trimethylsilyl and 2-tetrahydropyranyl.

A C$_1$-C$_6$ alkoxy group is, preferably, methoxy or ethoxy. When R$_1$ is a C$_1$-C$_6$ alkyl group as defined above under (b), it is, preferably, unsubstituted methyl or ethyl.

When R$_1$ is a C$_6$-C$_{10}$ aryl or C$_7$-C$_{10}$ aralkyl group as defined above under (c), it is, preferably, phenyl or, respectively, benzyl, each unsubstituted or ring substituted by methyl, chlorine, nitro, amino or hydroxy.

When R$_1$ is —OR$_2$ as defined above under (d), preferably it is a group —OR$_2$ wherein R$_2$ is hydrogen; C$_1$-C$_6$ alkyl, in particular methyl or ethyl; a $C_2$–$C_{12}$ aliphatic or aromatic carboxylic acyl, in particular the acyl group deriving from acetic, α-bromoacetic, propionic, heptanoic, dodecanoic or benzoic acid; or a hydroxy protecting group, in particular one of those previously specified.

When X is a straight or branched $C_1$–$C_6$ aliphatic hydrocarbon chain, it is, preferably, a straight or branched $C_1$–$C_4$ alkylene chain such as, for instance, —$CH_2$—, —$(CH_2)_2$—, —$(CH_2)_3$— or

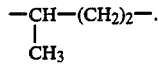

When Z is $C_1$–$C_6$ alkoxy, methoxy and ethoxy are preferred.

When Z is a group

wherein each of $R_3$ and $R_4$ is, independently, hydrogen or $C_1$–$C_6$ alkyl, it is, preferably, a group

wherein each of $R'_3$ and $R'_4$ is, independently, hydrogen or $C_1$–$C_4$ alkyl; preferred groups are —$NH_2$, —$NHCH_3$, —$NHC_2H_5$, —$N(CH_3)_2$ and —$N(C_2H_5)_2$.

When Z is a group

wherein $R_3$ and $R_4$, taken together with the nitrogen atom to which they are linked, form a pentatomic or hexatomic heteromonocyclic ring, this is, preferably, piperidino, piperazino, morpholino or thiomorpholino.

Pharmaceutically acceptable salts of the compounds of the invention are either salts with acids, either inorganic acids, such as, e.g., hydrochloric, sulfuric, phosphoric, hydrobromic or nitric, or organic acids, such as, e.g., acetic, formic, propionic, benzoic, maleic, malic, fumaric, succinic, tartaric, citric, oxalic, methanesulfonic or ethanesulfonic, or salts with bases, either inorganic bases, such as, e.g., sodium, potassium, calcium, aluminium hydroxides and alkali metal or alkaline-earth metal carbonates or bicarbonates, or organic bases, such as, e.g., organic amines or aminoacids, e.g. triethylamine, dibenzylamine, N-benzyl-3-phenethylamine, N,N-dibenzylethylenediamine, N-methylglucamine, trishydroxymethylaminomethane, lysine, procaine and the like.

In the formulae of this specification a dotted line ····· indicates a substituent in the α-configuration, i.e. below the plane of the ring; a wedged ▬ line indicates a substituent in the β-configuration, i.e. above the plane of the ring.

Where stereochemistry is unspecified, it is intended to include all the possible isomers, in particular α- and β-isomers, both separately and in mixture.

A preferred class of compounds according to the invention are the compounds of formula (I) wherein
$R_1$ is hydrogen or $C_1$–$C_4$ alkyl;
X is a direct bond or a straight or branched $C_1$–$C_4$ alkylene chain;
the symbol =Y represents

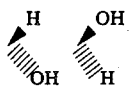

or =O;
Z is hydroxy, $C_1$–$C_6$ alkoxy or a group

wherein each of $R'_3$ and $R'_4$ is, independently, hydrogen or $C_1$–$C_4$ alkyl;
the symbol ═══ represents a single or double bond, the the pharmaceutically acceptable salts thereof.

Particularly preferred compounds in the ambit of this class are the compounds of formula (I) wherein $R_1$ is $C_1$–$C_4$ alkyl; X is a direct bond or a straight or branched $C_1$–$C_4$ alkylene chain; the symbol =Y represents =O; Z is $C_1$–$C_6$ alkoxy or a group

wherein each of $R_3'$ and $R_4'$ is, independently, hydrogen or $C_1$–$C_4$ alkyl; and the symbol ═══ represents a single or double bond.

In the above preferred class of compounds, when $R_1$ is $C_1$–$C_4$ alkyl, methyl and ethyl are preferred; when X is a straight or branched $C_1$–$C_4$ alkylene chain, the chain

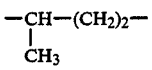

is preferred; preferred values for Z are methoxy, ethoxy, —$NH_2$, —$N(CH_3)_2$ and —$N(C_2H_5)_2$, in particular methoxy, —$N(CH_3)_2$ and —$N(C_2H_5)_2$.

Another preferred class of compounds according to the invention are the compounds of formula (I) wherein $R_1$ is —$OR_2$ wherein $R_2$ is hydrogen, $C_1$–$C_4$ alkyl or a $C_2$–$C_{12}$ aliphatic or aromatic carboxylic acyl or a hydroxy protecting group;
X is a direct bond or a straight or branched $C_1$–$C_4$ alkylene chain;
the symbol =Y represents

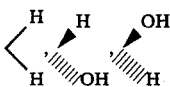

or =O;

Z is hydroxy or a group

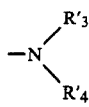

wherein each of $R'_3$ and $R'_4$ is, independently hydrogen or $C_1$–$C_4$ alkyl; and the symbol ═══ represents a single or double bond, and the pharmaceutically acceptable salts thereof.

Particularly preferred compounds in the ambit of this second preferred class are the compounds of formula (I) wherein $R_1$ is —$OR_2$ wherein $R_2$ is hydrogen, $C_1$–$C_4$ alkyl or a $C_2$–$C_{12}$ aliphatic carboxylic acyl group; X is a direct bond or a straight or branched $C_1$–$C_4$ alkylene chain;
the symbol =Y represents

Z is a group

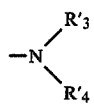

wherein each of $R'_3$ and $R'_4$ is, independently, hydrogen or $C_1$–$C_4$ alkyl, and the symbol ═══ represents a single or double bond.

In the ambit of the above preferred class of compounds, preferably $R_1$ is a group —$OR_2$ wherein $R_2$ is hydrogen, methyl or an acyl group chosen from acetyl, propionyl, heptanoyl and dodecanoyl; when X is a straight or branched $C_1$–$C_4$ alkylene chain, a preferred chain is

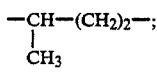

preferred values for Z are —$NH_2$, —$N(CH_3)_2$ and —$N(C_2H_5)_2$, in particular —$N(CH_3)_2$ and —$N(C_2H_5)_2$.

In this specification the compounds of formula (I) wherein X is

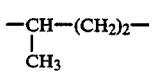

are referred to as cholane derivatives, more specifically as 4-aza-cholan-3-one-derivatives.

Examples of specific compounds preferred under this invention are:

(1) 24-N,N-diethylcarbamoyl-4-hydroxy-4-azachol-5-en-3-one;

(2) 24-N,N-dimethylcarbamoyl-4-hydroxy-4-azachol-5-en-3-one;

(3) 24-N,N-diethylcarbamoyl-4-hydroxy-4-aza-5α-cholan-3-one;

(4) 24-N,N-diethylcarbamoyl-4-hydroxy-4-aza-5β-cholan-3-one;

(5) 24-N,N-dimethylcarbamoyl-4-hydroxy-4-aza-5α-cholan-3-one;

(6) 24-N,N-dimethylcarbamoyl-4-hydroxy-4-aza-5β-cholan-3-one;

(7) 24-N,N-diethylcarbamoyl-4-methoxy-4-azachol-5-en-3-one;

(8) 24-N,N-dimethylcarbamoyl-4-methoxy-4-azachol-5-en-3-one;

(9) 24-N,N-diethylcarbamoyl-4-ethoxy-4-azachol-5-en-3-one;

(10) 24-N,N-dimethylcarbamoyl-4-ethoxy-4-azachol-5-en-3-one;

(11) 24-N,N-diethylcarbamoyl-4-methyl-4-azachol-5-en-3,12-dione;

(12) 24-N,N-diethylcarbamoyl-4-ethyl-4-azachol-5-en-3,12-dione;

(13) 24-N,N-dimethylcarbamoyl-4-methyl-4-azachol-5-en-3,12-dione;

(14) 24-N,N-dimethylcarbamoyl-4-ethyl-4-azachol-5-en-3,12-dione;

(15) 24-N,N-diethylcarbamoyl-4-methyl-4-azachol-5-en-12α-hydroxy-3-one;

(16) 17β-N,N-diethylcarbamoyl-4-hydroxy-4-azaandrost-5-en-3-one;

(17) 17β-N,N-diethylcarbamoyl-4-methoxy-4-azaandrost-5-en-3-one;

(18) 24-N,N-diethylcarbamoyl-4-methoxy-4-aza-5α-cholan-3-one;

(19) 24-N,N-diethylcarbamoyl-4-methoxy-4-aza-5β-cholan-3-one;

(20) 24-N,N-diethylcarbamoyl-4-methyl-4-aza-5α-cholan-3,12-dione;

(21) 24-methoxycarbonyl-4-methyl-4-aza-chol-5-en-3,12-dione, and

(22) 24-methoxycarbonyl-4-methyl-4-aza-5α-cholan-3,12-dione.

The structural formulae of the above listed compounds, according to their progressive number, are tabulated below with reference to the formula (I)

TABLE

| Compound | $R_1$ | bond ═══ | configuration of hydrogen in 5 position | Y | X | Z |
|---|---|---|---|---|---|---|
| 1 | OH | double | — | H, H | $-\underset{CH_3}{CH}-(CH_2)_2-$ | —$N(C_2H_5)_2$ |
| 2 | OH | double | — | H, H | $-\underset{CH_3}{CH}-(CH_2)_2-$ | —$N(CH_3)_2$ |

TABLE-continued

| Compound | $R_1$ | bond | configuration of hydrogen in 5 position | Y | X | Z |
|---|---|---|---|---|---|---|
| 3 | OH | single | α | H/ \H | $-CH(CH_3)-(CH_2)_2-$ | $-N(C_2H_5)_2$ |
| 4 | OH | single | β | H/ \H | $-CH(CH_3)-(CH_2)_2-$ | $-N(C_2H_5)_2$ |
| 5 | OH | single | α | H/ \H | $-CH(CH_3)-(CH_2)_2-$ | $-N(CH_3)_2$ |
| 6 | OH | single | β | H/ \H | $-CH(CH_3)-(CH_2)_2-$ | $-N(CH_3)_2$ |
| 7 | $OCH_3$ | double | — | H/ \H | $-CH(CH_3)-(CH_2)_2-$ | $-N(C_2H_5)_2$ |
| 8 | $OCH_3$ | double | — | H/ \H | $-CH(CH_3)-(CH_2)_2-$ | $-N(CH_3)_2$ |
| 9 | $OC_2H_5$ | double | — | H/ \H | $-CH(CH_3)-(CH_2)_2-$ | $-N(C_2H_5)_2$ |
| 10 | $OC_2H_5$ | double | — | H/ \H | $-CH(CH_3)-(CH_2)_2-$ | $-N(CH_3)_2$ |
| 11 | $CH_3$ | double | — | =O | $-CH(CH_3)-(CH_2)_2-$ | $-N(C_2H_5)_2$ |
| 12 | $C_2H_5$ | double | — | =O | $-CH(CH_3)-(CH_2)_2-$ | $-N(C_2H_5)_2$ |
| 13 | $CH_3$ | double | — | =O | $-CH(CH_3)-(CH_2)_2-$ | $-N(CH_3)_2$ |
| 14 | $C_2H_5$ | double | — | =O | $-CH(CH_3)-(CH_2)_2-$ | $-N(CH_3)_2$ |
| 15 | $CH_3$ | double | — | H, OH | $-CH(CH_3)-(CH_2)_2-$ | $-N(C_2H_5)_2$ |
| 16 | OH | double | — | H/ \H | bond | $-N(C_2H_5)_2$ |
| 17 | $OCH_3$ | double | — | H/ \H | bond | $-N(C_2H_5)_2$ |

TABLE-continued

| Compound | $R_1$ | bond | configuration of hydrogen in 5 position | Y | X | Z |
|---|---|---|---|---|---|---|
| 18 | $OCH_3$ | single | α | $\overset{H}{\underset{H}{>}}$ | $-CH(CH_3)-(CH_2)_2-$ | $-N(C_2H_5)_2$ |
| 19 | $OCH_3$ | single | β | $\overset{H}{\underset{H}{>}}$ | $-CH(CH_3)-(CH_2)_2-$ | $-N(C_2H_5)_2$ |
| 20 | $CH_3$ | single | α | =O | $-CH(CH_3)-(CH_2)_2-$ | $-N(C_2H_5)_2$ |
| 21 | $CH_3$ | double | — | =O | $-\blacktriangleleft CH(CH_3)-(CH_2)_2-$ | $-OCH_3$ |
| 22 | $CH_3$ | single | α | =O | $-\blacktriangleleft CH(CH_3)-(CH_2)_2-$ | $-OCH_3$ |

The compounds of formula (I) may be prepared by a process comprising
(1) reacting a compound of formula (II)

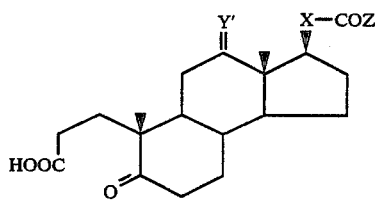
(II)

wherein X and Z are as defined above and Y' is =O,

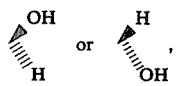

with a compound of formula (III)

$R'_1-NH_2$ (III)

wherein $R'_1$ has the meaning (a), (b) or (c) reported above for $R_1$, or a salt thereof, so obtaining a compound of formula (I) wherein $R_1$ is as defined above under (a), (b) or (c), the symbol ═══ represents a double bond, Y is =O

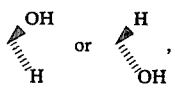

and X and Z are as defined above; or
(2) cyclizing a compound of formula (IV)

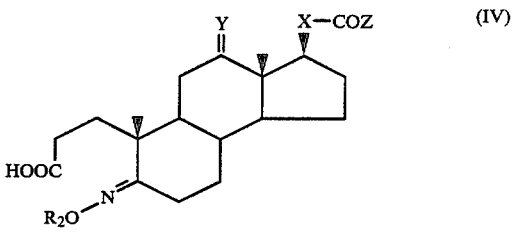
(IV)

wherein $R_2$, Y, X and Z are as defined above,
so obtaining a compound of formula (I) wherein $R_1$ is a group $-OR_2$ as defined above under (d), the symbol ═══ represents a double bond, and Y, X and Z are as defined above and, if desired, in any order, hydrogenating a compound of formula (I) wherein the symbol ═══ represents a double bond to obtain a corresponding compound of formula (I) wherein the symbol ═══ represents a single bond and/or, if desired, converting a compound of formula (I) into another compound of formula (I) and/or, if desired, converting a compound of formula (I) into a pharmaceutically acceptable salt thereof and/or, if desired, separating a mixture of isomers of formula (I) into the single isomers. A salt of a compound of formula (III) may be, for instance, the hydrochloride.

The reaction between a compound of formula (II) and a compound of formula (III) or a salt thereof may be, e.g., carried out in the presence of a base, either organic such as, for instance, pyridine or a tri-$C_1$-$C_6$ alkylamine, e.g. triethylamine, or inorganic such as, e.g. sodium or potassium hydroxide, operating in an inert solvent, such as, for example, methanol, ethanol, water, dioxane or diethyleneglycol. The reaction temperature is, preferably, between about 20° C. and about 150° C.

The cyclization of a compound of formula (IV) may be, e.g., performed by heating, for instance at a temperature between about 50° C. and about 150° C., in acetic or formic acid, optionally operating under reductive conditions, for example in the presence of zinc powder.

The optional hydrogenation of a compound of formula (I) wherein the symbol ═══ represents a double bond in order to obtain a corresponding compound of formula (I) wherein the symbol ===== represents a single bond may be, e.g., performed by treatment with hydrogen operating at a temperature which may vary from the room temperature to about 140° C. in a suitable solvent, such as, for example, acetic acid, dioxane or N,N-dimethylformamide, and in the presence of a suitable catalyst such as, for instance, platinum dioxide. The said hydrogenation leads to a mixture of 5α-H and 5β-H isomers which, if desired, may be separated into the single 5α-H and 5β-H compounds by conventional chromatography or fractional crystallization techniques.

Optional conversions of a compound of formula (I) into another compound of formula (I) include, for example, the conversion of a compound of formula (I) wherein Y is =O into a corresponding one wherein Y is

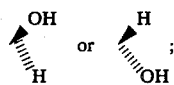

the conversion of a compound of formula (I) wherein $R_1$ is a group $OR_2$ where $R_2$ is hydrogen into a corresponding one wherein $R_1$ is a group $OR_2$ where $R_2$ is other than hydrogen; the conversion of a compound of formula (I) wherein Z is hydroxy into a corresponding one wherein Z is $C_1$-$C_6$ alkoxy or a group

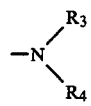

wherein $R_3$ and $R_4$ are as defined above; and also the conversion of a compound of formula (I) wherein the symbol ——— represents a single bond into a corresponding one wherein the said symbol represents a double bond.

The above said possible conversions may be carried out by known methods following conventional procedures. Thus, for example, a compound of formula (I) wherein Y is =O may be transformed into a corresponding compound wherein Y is

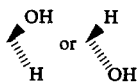

or hydrogenation in a suitable solvent at a suitable temperature in the presence of a conventional catalyst which may be, for instance, platinum dioxide: a possibly obtained mixture of epimeric α- and β-alcohols may be separated by fractional crystallization or chromatography.

The transformation of a compound of formula (I) wherein $R_1$ is $OR_2$ where $R_2$ is hydrogen into a corresponding compound of formula (I) wherein $R_1$ is a group —$OR_2$ wherein $R_2$ is a $C_1$-$C_6$ alkyl or $C_6$-$C_{10}$ aryl or $C_7$-$C_{10}$ aralkyl group as defined above for $R_1$ under (b) and (c), or a $C_2$-$C_{22}$ carboxylic acyl, may be carried out, e.g., by reaction with a compound of formula (V)

$$\text{Hal}—R'_2 \qquad (V)$$

wherein Hal is halogen, in particular bromine or chlorine, and $R'_2$ is a $C_1$-$C_6$ alkyl or $C_6$-$C_{10}$ aryl or $C_7$-$C_{10}$ aralkyl group as defined for $R_1$ under (b) and (c) or a $C_2$-$C_{22}$ carboxylic acyl.

Preferably the reaction is carried out in the presence of a basic agent which may be, for instance, an organic base such as, e.g., pyridine or triethylamine, operating at a temperature which may vary from the room temperature to about 100° C.

Alternatively a compound of formula (I) wherein $R_1$ is a group —$OR_2$ where $R_2$ is $C_1$-$C_6$ alkyl may also be obtained from the corresponding compound where $R_1$ is a group —$OR_2$ wherein $R_2$ is hydrogen by alkylation with a suitable diazoalkane: in this instance diethyl ether is preferably used as solvent at room temperature.

As an alternative approach too, a compound of formula (I) where $R_1$ is a group —$OR_2$ wherein $R_2$ is a $C_2$-$C_{22}$ carboxylic acyl may also be obtained from the corresponding compound where $R_1$ is —$OR_2$ wherein $R_2$ is hydrogen, by reaction with the desired $C_2$-$C_{22}$ carboxylic acid or a reactive derivative thereof such as the anhydride.

The optional conversion of a compound of formula (I) wherein $R_1$ is a group —$OR_2$ where $R_2$ is hydrogen into a corresponding one wherein $R_1$ is a group —$OR_2$ where $R_2$ is a hydroxy protecting group, e.g. of the kind previously specified, may be performed by methods known per se, according to standard etherification procedures.

The optional transformation of a compound of formula (I) wherein Z is hydroxy into a corresponding one wherein Z is $C_1$-$C_6$ alkoxy or a group

may be performed by conventional esterification or amidation reactions, and known methods may also be followed for converting a compound of formula (I) wherein the symbol ===== represents a single bond into a corresponding one wherein the symbol ===== represents a double bond.

Standard procedures may be used as well for converting a compound of formula (I) into a pharmaceutically acceptable salt thereof and conventional methods such as, e.g., fractional crystallization or chromatography, may be employed for separating a mixture of isomers of formula (I) into the single isomers.

The compounds of formula (II) are known compounds or may be prepared by known methods from known compounds. The compounds of formula (IV) may be prepared reacting a compound of formula (VI)

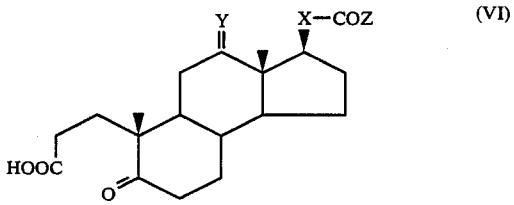

wherein Y, X and Z are as defined above, with a compound of formula (VII)

$$H_2N—OR_2 \qquad (VII)$$

wherein $R_2$ is as defined above, or a salt thereof, which may be, for instance, the hydrochloride. The reaction may be performed under conditions similar to those reported before for the analogous reaction between a compound of formula (II) and a compound of formula (III).

The compounds having the formulae (III), (V), (VI) and (VII) are known compounds or may be prepared by known methods from known compounds.

If required, any reactive functional group possibly present in any of the compounds involved in the above described reactions, may be conventionally protected before the reaction and then removed, in a conventional way too, at the end of the reaction itself.

As already said, the compounds of the invention are potent antiandrogens because of their ability to inhibit testosterone 5α-reductase. Thus, for example, the inhibitory effect of the compounds of the invention on 5α-reductase was determined in vitro in comparison with prosgesterone taken as the reference compound, according to the procedure reported herebelow.

Bioassay of 5α-reductase inhibitors

5α-reductase activity was evaluated using a combined mixture of nuclear, microsomal and mitrochondrial fractions (particulate fraction) from rat ventral prostate homogenates as the enzyme source. The particulate fraction was prepared centrifuging prostate homogenate at 140,000×g. The resulting pellet, washed several times, was resuspended in buffer and stored at −80° C. in aliquots containing 50 mg protein/ml.

The assay for 5α-reductase was done in a final volume of 0.5 ml containing 1 mM dithiothreitol, 40 mM sodium phosphate pH 6.5, 0.5 mM NADPH, 1 μM [$^{14}$C]-testosterone and 1 mg of prostate particulate fraction. The reaction mixture, after 30 min. incubation at 37° C., with or without the inhibitory compound, was extracted with ethyl acetate. The residue of the organic phase, resuspended in ethyl acetate, was chromatographed on silica gel plate using chloroform, acetone and n-hexane (2:1:2) as developing solvent system.

The t.l.c. plates were scanned for radioactivity and the area of unreacted testosterone and of 5α-reduced metabolites (5α-dihydrotestosterone, 3α- and 3β-diols) were measured. The concentrations of each compound that gave 50% inhibition (IC$_{50}$) of 5α-reductase was calculated. As reference compound progesterone was used and the potency of each compound was compared to progesterone (potency=1 by definition) using the formula $$\text{relative potency} = \frac{IC_{50} \text{ for progesterone}}{IC_{50} \text{ for the test compound}}.$$

The following table summarizes the results in activity obtained for the compounds of the invention identified by the numbers 1, 3, 4, 11, 15, 16 and 20 hereinbefore, in comparison with the reference compound progesterone:

| Compound | Relative potency |
|---|---|
| Progesterone | 1 |
| compound 1 | 43 |
| compound 3 | 32 |
| compound 4 | 13 |
| compound 11 | 16 |

-continued

| Compound | Relative potency |
|---|---|
| compound 15 | 13 |
| compound 16 | 10 |
| compound 20 | 32 |

It is evident from the reported data that the compounds of the invention are more potent 5α-reductase inhibitors than the reference compound. In view of the above indicated activity the compounds of the invention are therapeutically useful in the situations in which a decrease in androgen action, by means of 5α-reductase inhibition, is desirable such as, for example, benign prostatic hypertrophy, prostatic and breast cancers and certain skin-hair conditions such as, e.g., acne, seborrhoea, female hyrsutism and male pattern baldness. The toxicity of the compounds of the invention is quite negligible so that they can be safely used in therapy.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion; topically, e.g. in the form of creams. The dosage depends on the age, weight, conditions of the patient and administration route; for example the dosage adopted for oral administration to adult humans may range from about 20 to about 400 mg pro dose, from 1 to 5 times daily.

As already said the invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form. For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be, e.g. syrups, emulsions and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or, preferably, they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin. Conventional carriers may be used for topical formulations. The following examples illustrate but do not limit the invention.

The abbreviations DMF, t.l.c. and AcOH stand, respectively, for dimethylformamide, thin layer chromatography, and acetic acid.

The reported NMR data were determined in $CDCl_3$.

EXAMPLE 1

24-N,N-diethylcarbamoyl-5β-cholan-3-one

To a solution of 3-oxo-5β-cholan-24-oic acid [Burcknardt, T. Reichstein, Helv. Chim. Acta 25, 1434 (1942)] (16 g, 0.043 mol) in anhydrous benzene (250 ml), anhydrous pyridine (4.35 ml, 0.054 mol), followed by a solution of oxalyl chloride (4.7 ml, 0.054 mol) in benzene (10 ml), were added dropwise. After stirring at room temperature for 1 hour, the solution was cooled to 10° C. and the pH adjusted to persistent alkaline by slowly adding a 1/1 solution of N,N-diethylamine in benzene. The resulting solution was stirred for 30 minutes, poured into ice-water and extracted with ethyl acetate. The organic layers were washed with dilute HCl and dried. The solvent was removed in vacuo, obtaining an amorphous solid, which was recrystallized from ligroin to yield the title compound (14 g), m.p. 113°–114° C.;

Elemental analysis: Calculated for $C_{28}H_{47}NO_2$: C 78.27; H 11.03; N 3.26; found: C 78.39; H 11.01; N 3.25; m/z 429 (M+), 414, 156;

I.R. (nujol): 1715, 1650 $cm^{-1}$;

$^1H$ NMR: 3.35 (m, 4H, $N(CH_2CH_3)_2$;

$^{13}C$ NMR: 213.1 (C-3), 172.6 (C-24), 42.0–40.1 (N—$(CH_2$—$)_2$, 22.7 (C-19), 18.5 (C-21), 14.5–13.1 (N—$CH_2$—$CH_3)_2$, 12.1 (C-18).

By analogous procedure, 24-N,N-dimethylcarbamoyl-5β-cholan-3-one was obtained.

EXAMPLE 2

24-N,N-diethylcarbamoyl-chol-4-en-3-one

To a well stirred solution of 24-N,N-diethylcarbamoyl-5β-cholan-3-one (16.4 g, 0.038 mol) in chloroform (200 ml), a solution of bromine (2.2 ml, 0.043 mol) in the same solvent (10 ml) was added dropwise at room temperature and the stirring was continued until colourless solution. At this time the solvent was stripped off, the residue was dissolved in DMF (150 ml) and LiCl (16.2 g, 0.38 mol) was added. The resulting mixture was heated at 110° C. with stirring overnight. The reaction mixture was poured into ice-water, acidified with diluted HCl, extracted with ethyl acetate and dried. The solvent was removed in vacuo and the residue chromatographed at medium pressure eluting with ethyl acetate n-hexane 1/1, obtaining the title compound as crystalline solid (7.5 g), m.p. 113°–115° C.;

Elemental analysis: Calculated for $C_{28}H_{45}NO_2$: C 78.64; H 10.61; N 3.28; Found: C 78.50; H 10.60; N 3.27; m/z 427 (M+), 412, 313, 271, 156;

I.R. (nujol): 1675, 1650 $cm^{-1}$;

$^1H$ NMR: 5.75 (s, 1H), 3.35 (m, 4H, N—$CH_2$—$)_2$;

$^{13}C$ NMR: 199.4 (C-3), 172.6 (C-24), 171.5 (C-5), 123.8 (C-4), 42.0–40.0 (N—C), 18.5 (C-21), 17.4 (C-19), 14.5–13.1 (N—$CH_2$—C), 12.0 (C-18).

By analogous procedure 24-N,N-dimethylcarbamoyl-chol-4-en-3-one was obtained.

EXAMPLE 3

24-N,N-diethylcarbamoyl-5-oxo-3,5-seco-4-nor-cholan-3-oic acid

To a stirred solution of 24-N,N-diethylcarbamoyl-chol-4-en-3-one (2 g, 0.0047 mol) in tert.butyl alcohol (52 ml) containing sodium carbonate (0.74 g, 0.007 mmol, dissolved in 3.5 ml of water), a solution of sodium periodate (6.95 g, 0.032 mol) in water (52 ml) and a solution of potassium permanganate (3.9 ml of 2% aqueous solution) were added dropwise simultaneously at a temperature between 25° and 40° C. and at a rate sufficient to keep the solution light pink. The solution was stirred for 2 hours, filtered and the filtrate was concentrated to small volume in order to eliminate the tert.butyl alcohol. The resulting residue was acidified at 0° C. with $H_2SO_4$ (50% aqueous solution) and extracted with ethyl acetate. The organic layers were washed with potassium hydrogen sulfate, dried ($Na_2SO_4$) and the solvent removed in vacuo. The residue was chromatographed (ethyl acetate as eluant) to give the title compound (1.2 g), m.p. 152°–155° C.;

Elemental analysis: Calculated for $C_{27}H_{45}NO_4$: C 72.44; H 10.13; N 3.13; Found: C 72.54; H 10.11; N 3.12; m/z 447 (M+), 382, 156;

I.R. (nujol): 3200, 1730, 1695 $cm^{-1}$;

$^1H$ NMR: 9.1 (bs, 1H), 3.35 (m, 4H, N—$(CH_2$—$)_2$).

By analogous procedure 24-N,N-dimethylcarbamoyl-5-oxo-3,5-seco-4-nor-cholan-3-oic acid was obtained.

EXAMPLE 4

24-N,N-diethylcarbamoyl-3,5-seco-4-nor-cholan-5-hydroxy-imino-3-oic acid

To a solution of 24-N,N-diethylcarbamoyl-5-oxo-3,5-seco-4-nor-cholan-3-oic acid (3 g, 0.0067 mol) in ethanol (90 ml of 95% solvent), potassium hydroxide (60 ml of a 5% aqueous solution) and hydroxylamine hydrochloride (0.9 g, 0.0129 mol) were added. After refluxing for 2 hours, the volume was concentrated to a half and the solution was acidified with acetic acid. The reaction mixture was extracted with ethyl acetate, dried, the solvent removed in vacuo and the residue crystallized from ethyl acetate to give the title compound (2.15 g), m.p. 163°–165° C.;

Elemental analysis: Calculated for $C_{27}H_{46}N_2O_4$: C 70.09; H 10.02; N 6.05; Found: C 70.18; H 10.01; N 6.06; m/z 462 (M+), 444, 427;

I.R. (nujol): 3420, 3200, 1745, 1705, 1595, 930 $cm^{-1}$;

$^1H$ NMR: 8.45 (bs, 1H), 3.35 (m, 4H, N—$(CH_2$—$)_2$);

$^{13}C$ NMR: 178.4 (C-3), 173.3 (C-24), 164.0 (C-5), 22.0 (C-19), 18.5 (C-21), 14.4–13.1 (N—$(CH_2C)_2$), 12.0 (C-18).

By analogous procedure 24-N,N-dimethylcarbamoyl-3,5-seco-4-nor-cholan-5-hydroxy-imino-3-oic acid was prepared.

EXAMPLE 5

24-N,N-diethylcarbamoyl-4-hydroxy-4-azachol-5-en-3-one

(compound 1)

To a solution of 24-N,N-diethylcarbamoyl-3,5-seco-4-nor-cholan-5-hydroxyimino-3-oic acid (1.55 g, 0.0033 mol) in acetic acid (44 ml), powdered Zn (2.4 g, 0.036 mol) was added portionwise. The mixture was stirred vigorously heating at 90°–95° C. for 1 hour. The suspension was filtered off. The filtrate was diluted with water to give a white solid which was filtered, dried in dryseal dessicator, and purified by a column chromatography (ethyl acetate/methanol 98/2 as eluant). The product was recrystallized from methanol to yield the title compound (0.73 g), m.p. 215°–218° C.;

Elemental analysis: Calculated for $C_{27}H_{44}N_2O_3$: C 72.93; H 9.97; N 6.30; Found: C 73.06; H 9.99; N 6.29;
m/z 444 (M+), 427, 330, 314, 156;
I.R. (nujol): 1650 cm$^{-1}$;
$^1$H NMR: 5.52 (s, 1H), 3.35 (m, 4H);
$^{13}$C NMR: 172.7 (C-24), 161.7 (C-3), 139.0 (C-5), 104.0 (C-6), 42.1–40.1 (N—($\underline{C}$)$_2$), 19.0 (C-19), 18.6 (C-21), 14.5–13.1 (N—(CH$_2$—$\underline{C}$)$_2$), 12.0 (C-18).

By analogous procedure 24-$\overline{N}$,N-dimethylcarbamoyl-4-hydroxy-4-azachol-5-en-3-one (compound 2) was prepared.

EXAMPLE 6

24-N,N-diethylcarbamoyl-4-hydroxy-4-aza-5α-cholan-3-one

(compound 3) and

24-N,N-diethylcarbamoyl-4-hydroxy-4-aza-5β-cholan-3-one

(compound 4)

A solution of 24-N,N-diethylcarbamoyl-4-hydroxy-4-azachol-5-en-3-one (1 g, 0.0022 mol) in acetic acid (56 ml) was hydrogenated for 5 hours over PtO$_2$ (0.25 g, 0.0011 mol) at H$_2$ pressure of 40 psi. After filtration to remove catalyst, the reaction mixture was concentrated under high vacuum and the residue crystallized from benzene/petroleum ether. A t.l.c. of the solid showed two spots. Separation of the corresponding compounds by preparative t.l.c. gave the 5β-isomer (compound 4) (0.4 g), m.p. 125°–128° C.;

Elemental analysis: Calculated for $C_{27}H_{46}N_2O_3$: C 72.60; H 10.38; N 6.27; Found: C 72.49; H 10.39; N 6.26;
m/z 446 (M+), 431, 322, 316, 302, 156;
I.R. (nujol): 1640 cm$^{-1}$;
$^{13}$C NMR: 172.7 (C-24), 164.7 (C-3), 21.3 (C-19), 18.6 (C-21), 14.5–13.1 (N—(CH$_2$—$\underline{C}$)$_2$, 12.0 (C-18).

From the mother liquor after standing overnight, a new solid was obtained. This product was identified as the 5α-isomer (compound 3), (0.2 g), m.p. 228°–230° C.;

Elemental analysis: Calculated for $C_{27}H_{46}N_2O_3$: C 72.60; H 10.38. N 6.27; Found: C 72.73; H 10.40; N 6.28;
m/z 446 (M+), 431, 322, 316, 302, 156;
I.R. (nujol): 1640 cm$^{-1}$;
$^1$NMR: 8.05 (bs, 1H), 3.5 (m, 4H);
$^{13}$C NMR: 172.7 (C-24), 165.5 (C-3), 18.5 (C-21), 14.5–13.1 (N—(CH$_2$—$\underline{C}$)$_2$), 12.5 (C-19), 12.0 (C-18).

By analogous procedure the following compounds were obtained:
24-N,N-dimethylcarbamoyl-4-hydroxy-4-aza-5α-cholan-3-one (compound 5);
24-N,N-dimethylcarbamoyl-4-hydroxy-4-aza-5β-cholan-3-one (compound 6);
24-N,N-diethylcarbamoyl-4-methoxy-4-aza-5α-cholan-3-one (compound 18), m.p. 180°–182° C.;
24-N,N-diethylcarbamoyl-4-methoxy-4-aza-5β-cholan-3-one (compound 19), m.p. 108°–110° C.;
24-N,N-diethylcarbamoyl-4-methyl-4-aza-5α-cholan-3,12-dione (compound 20);
24-methoxycarbonyl-4-methyl-4-aza-5α-cholan-3,12-dione (compound 22), m.p. 132°–133° C.

EXAMPLE 7

24-N,N-diethylcarbamoyl-4-methoxy-4-aza-5α-cholan-3-one (compound 18)

To a suspensione of KH (0.2 g, 20% suspension in paraffin) in anhydrous tetrahydrofuran (15 ml) a solution of 24-N,N-diethylcarbamoyl-4-hydroxy-4-aza-5α-cholan-3one (0.2 g, 0.45 mmol) was added. The solution was heated at 40° C. then a solution of methyl iodide (0.2 ml) in tetrahydrofuran (10 ml) was added thereto. After stirring 20 minutes at 50° C., the reaction mixture was cooled to 0° C., acidified with diluted (1:1) aqueous hydrochloric acid and extracted with ethylacetate; the organic layers were washed with brine, dried over Na$_2$SO$_4$, and the solvent removed in vacuo. The residue was chromatographed (ethyl acetate/CH$_3$OH 97/3 as eluant) to give the title compound in quantitative yield, m.p. 180°–182° C.

Elemental analysis: Calculated for $C_{28}H_{48}N_2O_3$: C 73.00; H 10.5; N 6.08; Found: C 73.09; H 10.48; N 6.07;
m/z 460 (M+), 445, 429, 346, 333, 316, 300;
I.R. (nujol): 1700, 1635 cm$^{-1}$;
$^1$H NMR: 3.75 (s, 3H); 3.35 (m, 5H);
$^{13}$C NMR: 172.6 (C-24); 168.6 (C-3); 62.8 (O—CH$_3$); 18.6 (C-21); 14.4–13.3 (N—CH$_2$—C)$_2$; 12.6 (C-19); 12.3 (C-18).

By analogous procedure there was obtained 24-N,N-diethylcarbamoyl-4-methoxy-4-aza-5β-cholan-3-one (compound 19), m.p. 108°–110° C.;
m/z 460 (M+), 445, 429, 346, 333, 316.
I.R. (nujol): 1660; 1635 cm$^{-1}$;
$^1$H NMR: 375 (s, 3H); 3.35 (m, 5H);
$^{13}$C NMR: 172.6 (C-24), 168.1 (C-3), 61.3 (OCH$_3$), 21.8 (C-19); 18.6 (C-21), 14.3–13.3 (CH$_2$—$\underline{C}$H3), 12.1 (C-18).

EXAMPLE 8

24-methoxycarbonyl-4-methyl-4-azachol-5-en-3,12-dione

(compound 21)

A solution of 5,12-dioxo-3,5-seco-4-nor-cholan-3-carboxy-24-oic acid (3 g, 0.0074 mol) in anhydrous ethanol (20 ml) saturated with N-methylamine, was heated in sealed tube at 125° C. overnight. The solvent was removed, methanol (100 ml) and BF$_3$ etherate were added. The resulting solution was refluxed for 3 hours, cooled to 10° C., decomposed with ice-water and extracted with chloroform. The organic layers were washed with water, brine, dried and the solvent removed in vacuo. Chromatography of the resulting residue (ethylacetate as eluant), gave the title compound (1.3 g, 42%), m.p. 136°–138° C.;

Elemental analysis: Calculated for $C_{25}H_{37}NO_4$: C 72.26; H 8.97; N 3.37; Found: C 72.13; H 8.97; N 3.38;
m/z 415 (M+), 400, 258;
I.R. (nujol): 1750, 1710, 1680, 1635 cm$^{-1}$;

$^1$H NMR: 5.15 (m, 1H); 3.7 (s, 3H); 3.15 (s, 3H);
$^{13}$C NMR: 213.3 (C-12); 174.4 (C-24); 168.0 (C-3); 144.3 (C-5); 104.0 (C-6); 51.3 (O-CH$_3$); 18.6 (C-22); 18.6 (C-19); 11.8 (C-18).

EXAMPLE 9

24-methoxycarbonyl-4-methyl-4-aza-5α-cholan-3,12-dione (compound 22)

A solution of 24-methoxycarbonyl-4-methyl-4-aza-chol-5-en-3,12 dione (0.5 g) in acetic acid (50 ml), was hydrogenated for 5 hours over PtO$_2$ (0.25 g) (pH$_2$ 40 psi). After filtration to remove the catalyst, the reaction mixture was concentrated under high vacuum and the residue dissolved in ethyl acetate and chromatographed. The 5α isomer was oxidated by Johnson procedure [J.A.C.S. 73, 5464, (1951)] to give, after chromatography, the title compound (0.2 g, 40%), m.p. 132°–133° C.

Elemental analysis: Calculated for C$_{25}$H$_{39}$NO$_4$: C 71.9; H 9.41; N 3.35; Found: C 72.01; H 9.4; N 3.35; m/z 417 (M+), 262

I.R. (nujol): 1735, 1710, 1650 cm$^{-1}$;
$^1$H NMR: 3.7 (s, 3H); 3.00 (s, 3H);
$^{13}$C NMR: 213.4 (C-12); 174.5 (C-24); 170.5 (C-3); 51.4 (OCH$_3$); 18.7 (C-21); 12.1 (C-9); 11.8 (C-18).

EXAMPLE 10

24-N,N-diethylcarbamoyl-4-methoxy-4-azachol-5-en-3-one (compound 7)

To an ethereal suspension of 24-N,N-diethylcarbamoyl-4-hydroxy-4-azachol-5-en-3-one (1 g, 0.0026 mol), a solution of diazomethane in diethyl ether was added dropwise at 0° C., monitoring by t.l.c., until the starting material disappeared. At this time few drops of AcOH were added, the solvent was stripped off and the residue chromatographed on silica gel eluting with ethyl acetate/methanol 97/3 to obtain a solid, which was crystallized from methanol-water to give the title compound (0.6 g), m.p. 154°–156° C.;

Elemental analysis: Calculated for C$_{28}$H$_{46}$N$_2$O$_3$: C 73.32; H 10.11; N 6.11 Found: C 73.44; H 10.10; N 6.10; m/z 458 (M+), 428, 314, 156;
$^1$H NMR: 5.45 (m, 1H), 3.70 (s, 3H), 3.35 (m, 4H);
$^{13}$C NMR: 172.3 (C-24), 162.8 (C-3), 139.0 (C-5), 102.1 (C-6), 41.7–39.8 (N-(C)$_2$), 35.4 (O-CH$_3$), 18.6 (C-19), 18.3 (C-21), 14.2–12.9 (N-(CH$_2$-C)$_2$), 11.7 (C-18).

By analogous procedure the following compounds were obtained:
24-N,N-dimethylcarbamoyl-4-methoxy-4-azachol-5-en-3-one (compound 8);
24-N,N-dimethylcarbamoyl-4-ethoxy-4-azachol-5-en-3-one (compound 9);
24-N,N-dimethylcarbamoyl-4-ethoxy-4-azachol-5-en-3-one (compound 10).

EXAMPLE 11

24-N,N-diethylcarbamoyl-4-methyl-4-azachol-5-en-3,12-dione (compound 11)

A solution of 5,12-dioxo-3,5-seco-4-nor-cholan-3-carboxy-24-oic acid (3 g, 0.0074 mol) in anhydrous ethanol (33 ml) saturated with N-methylamine, was heated in sealed tube at 125° C. overnight. The solvent was removed and pyridine (0.76 ml, 0.0094 mol) in CHCl$_3$ (70 ml) was added. To this well stirred solution, oxalyl chloride (0.81 ml, 0.0094 mol) in CHCl$_3$ (8 ml) was added dropwise. The resulting solution was stirred for 1 hour at room temperature, cooled to 10° C. and the pH adjusted to persistent alkaline by adding N,N-diethyl amine in CHCl$_3$. The mixture was stirred for further 30 minutes, decomposed with ice-water and extracted with chloroform. The organic layers were washed with water, brine, dried and the solvent removed in vacuo. Chromatography of the resulting residue, with ethylacetate as eluant, and crystallization from ethyl acetate gave the title compound (2 g), m.p. 196°–199° C.;

Elemental analysis: Calculated for C$_{28}$H$_{44}$N$_2$O$_3$: C 73.64; H 9.71; N 6.13; Found: C 73.53; H 9.69; N 6.18; m/z 456 (M+), 441, 342, 156;
I.R. (nujol): 1710, 1675, 1645 cm$^{-1}$;
$^1$H NMR: 5.15 (m, 1H), 3.35 (m, 4H), 3.15 (s, 3H);
$^{13}$C NMR: 213.9 (C-12), 172.5 (C-24), 168.0 (C-3), 143.9 (C-5), 104.3 (C-6), 42.0–40.1 (N-(CC-)$_2$), 31.0 (N-CH$_3$), 18.8 (C-19), 18.5 (C-21), 14.4–13.1 (N-(CH$_2$-C)$_2$), 11.8 (C-18).

By analogous procedure the following compounds were prepared:
24-N,N-diethylcarbamoyl-4-ethyl-4-azachol-5-en-3,12-dione (compound 12);
24-N,N-dimethylcarbamoyl-4-methyl-4-azachol-5-en-3,12-dione (compound 13);
24-N,N-dimethylcarbamoyl-4-ethyl-4-azachol-5-en-3,12-dione (compound 14).

EXAMPLE 12

24-N,N-diethylcarbamoyl-4-methyl-4-azachol-5-en-12α-hydroxy-3-one (compound 15)

24-N,N-diethylcarbamoyl-4-methyl-4-azachol-5-en-3,12-dione (1.35 g, 0.00296 mol) was dissolved in acetic acid (100 ml) and hydrogenated using Parr apparatus (at the H$_2$ pressure of 40 psi) for 12 hours using PtO$_2$ (0.25 g, 0.0011 mol) as catalyst. The catalyst was removed by filtration, the filtrate was diluted with chloroform, neutralized with NaHCO$_3$ (10% aqueous solution) and extracted with chloroform. The organic layers were washed with water, brine, dried, and the solvent removed in vacuo. Separation with column chromatography (ethyl acetate/methanol as eluant) followed by crystallization from n-hexane-ethyl acetate gave the title compound (0.4 g), m.p. 166°–170° C., Elemental analysis: Calculated for C$_{28}$H$_{46}$N$_2$O$_3$: C 73.32; H 10.11; N 6.11; Found: C 73.23; H 10.09; N 6.13; m/z 458 (M+), 440, 425, 344, 307, 156;
I.R. (nujol): 3420, 1675, 1650, 1620 cm$^{-1}$;
$^1$H NMR: 5.1 (m, 1H), 4.1 (bt, 1H), 3.35 (m, 4H), 3.15 (s, 3H);
$^{13}$C NMR: 172.6 (C-24), 168.4 (C-3), 144.2 (C-5), 104.7 (C-6), 72.9 (C-12), 18.7 (C-19), 17.7 (C-21), 14.5–13.1 (N-(CH$_2$-C)$_2$), 12.8 (C-18).

EXAMPLE 13

24-N,N-diethylcarbamoyl-5-methoxyimino-3,5-seco-4-nor-cholan-3-oic acid

To a solution of 24-N,N-diethylcarbamoyl-5-oxo-3,5-seco-4-nor-cholan-3-oic acid (0.5 g, 0.0011 mol) in pyridine (5 ml), methoxyamine hydrochloride (0.12 g, 0.0014 mol) was added. After being stirred at room temperature overnight, the solution was decomposed with water, acidified with diluted HCl, and extracted with chloroform. Usual work-up, followed by purification with column chromatography (ethyl acetate/n-hexane 7/3 as eluant) and crystallization from ethyl acetate yielded the title compound (0.45 g), m.p. 158°-159° C.;

Elemental analysis: Calculated for $C_{28}H_{48}N_2O_4$: C 70.55; H 10.15; N 5.88; Found: C 70.47; H 10.16; N 5.92; m/z 476 (M+), 445, 417, 404, 362, 156;

I.R. (nujol): 3300, 1730, 1620 cm$^{-1}$;

$^1$H NMR: 9.0 (bs, 1H), 3.8 (s, 3H), 3.35 (m, 4H).

By analogous procedure the following compounds were obtained:

24-N,N-diethylcarbamoyl-5-ethoxyimino-3,5-seco-4-nor-cholan-3-oic acid;

24-N,N-dimethylcarbamoyl-5-methoxyimino-3,5-seco-4-nor-cholan-3-oic acid;

24-N,N-dimethylcarbamoyl-5-ethoxyimino-3,5-seco-4-nor-cholan-3-oic acid.

EXAMPLE 14

24-N,N-diethylcarbamoyl-4-methoxy-4-azachol-5-en-3-one (compound 7)

Refluxing of 24-N,N-diethylcarbamoyl-5-methoxyimino-3,5-seco-4-nor-cholan-3-oic acid in acetic acid for 8 hours gave with 30% yield the title compound, which resulted identical in all respects to the product obtained in example 10. By analogous procedure also the compounds 8, 9 and 10 were prepared.

EXAMPLE 15

17β-N,N-diethylcarbamoyl-3,5-seco-4-nor-androstan-5-hydroxyimino-3-oic acid

To a solution of 17β-N,N-diethylcarbamoyl-5-oxo-3,5-seco-4-nor-androstan-3-oic acid (3 g, 0.0076 mol) in ethanol (95%), was added KOH (70 mol of 5% aqueous solution) followed by hydroxylamine hydrochloride (1.05 g, 0.015 mol). The solution was refluxed for 3 hours. After acidification with acetic acid a white precipitate was obtained. Recrystallization from MeOH gave the title compound (2.1 g), m.p. 223°-225° C.;

Elemental analysis: Calculated for $C_{23}H_{38}N_2O_4$: C 67.95; H 9.42; N 6.89; Found: C 68.05; H 9.41; N 6.88; m/z 406 (M+), 389, 388, 372, 357, 176;

I.R. (nujol): 3400, 3200, 1750, 1590 cm$^{-1}$;

$^1$H NMR: 7.0 (m, 2H), 3.7 (m, 2H), 3.15 (m, 2H).

By analogous procedure, 17β-N,N-diethylcarbamoyl-3,5-seco-4-nor-androstan-5-methoxyimino-3-oic acid was prepared.

EXAMPLE 16

17β-N,N-diethylcarbamoyl-4-hydroxy-4-aza-androst-5-en-3-one (compound 16)

A solution of 17β-N,N-diethylcarbamoyl-3,5-seco-4-nor-androstan-5-hydroxyimino-3-oic acid (4.06 g, 0.01 mol) in acetic acid was refluxed for 4 hours. The reaction mixture was poured into ice-water, neutralized with NaHCO$_3$ and extracted with diethyl ether. The solvent was stripped off and a white solid was obtained. Recrystallization of the residue from ethyl acetate gave the title compound (2.83 g), m.p. 194°-198° C.;

Elemental analysis: Calculated for $C_{23}H_{36}N_2O_3$: C 71.1; H 9.34; N 7.21; Found: C 70.98; H 9.33; N 7.26; m/z 388 (M+), 371, 357;

I.R. (nujol): 3150, 1640 cm$^{-1}$;

$^1$H NMR: 8.0 (bs, 1H), 5.55 (m, 1H), 3.7 (m, 2H), 3.15 (m, 2H), 2.6 (m, 3H);

$^{13}$C NMR: 172.2 (C-17), 161.3 (C-3), 138.5 (C-5), 103.9 (C-6), 19.0 (C-19), 14.7-14.1 (N-(CH$_2$C)$_2$), 14.0 (C-18).

By analogous procedure, 17β-N,N-diethylcarbamoyl-4-methoxy-4-aza-androst-5-en-3-one (compound 17) was prepared.

EXAMPLE 17

Scored tablets for oral use, each containing 250 mg of the active substance, were manufactured as follows:

| Composition (for 10,000 tablets) | |
|---|---|
| 24-N,N—diethylcarbamoyl-4-hydroxy-4-azachol-5-en-3-one | 2500 g |
| corn starch | 275 g |
| talc powder | 187 g |
| calcium stearate | 38 g |

The active substance was granulated with a 4% w/v aqueous solution of methyl cellulose. To the dried granules a mixture of the remainder of the ingredients is added and the final mixture compressed into tablets of proper weight.

EXAMPLE 18

Two-piece hard gelatin capsules for oral use, each containing 250 mg of active substance were manufactured as follows.

| Composition for 10,000 capsules | |
|---|---|
| 24-N,N—diethylcarbamoyl-4-hydroxy-4-aza-5α-cholan-3-one | 2500 g |
| lactose | 1000 g |
| corn starch | 300 g |
| talc powder | 65 g |
| calcium stearate | 35 g |

The active substance was mixed with the starch-lactose mixture followed by the talc and calcium stearate. The final mixture was encapsulated in the conventional manner.

We claim:

1. A compound of the following formula (I)

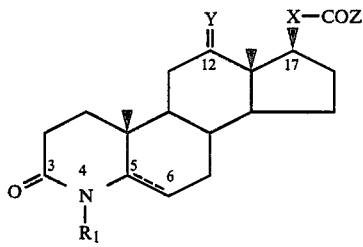

wherein
R$_1$ is
(a) hydrogen;
(b) C$_1$-C$_6$ alkyl unsubstituted or substituted by a substituent chosen from carboxy, halogen and amino;
(c) a phenyl, α-naphthyl, β-naphthyl or benzyl group, either unsubstituted or ring substituted by a substituent chosen from C$_1$-C$_6$ alkyl, halogen, nitro, amino and hydroxy, or (d) —OR$_2$ wherein R$_2$ either has one of the meanings (a), (b) and (c) reported above for R$_1$; or is a C$_2$–C$_{12}$-aliphatic or aromatic carboxylic acyl or a hydroxy protecting group chosen from the group consisting of dimethyltert butyl silyl, trimethylsilyl, and 2-tetrahydropyranyl;

X is direct bond or a straight or branched C$_1$–C$_6$-aliphatic hydrocarbon chain;

the symbol =Y represents

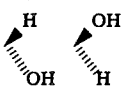

or =O;

Z is
(a') hydroxy;
(b') C$_1$–C$_6$ alkoxy; or
(c')

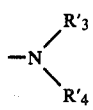

wherein each of R$_3$ and R$_4$ is, independently, hydrogen or C$_1$–C$_6$ alkyl; or R$_3$ and R$_4$ taken together with the nitrogen atom to which they are linked, from a hexatomic heteromonocyclic ring chosen from piperidino, piperazino, morpholino and thiomorpholino;

the symbol ═══ represents a single or double bond, and the pharmaceutically acceptable salts thereof.

2. C compound of formula (I) according to claim 1, wherein R$_1$ is hydrogen or C$_1$–C$_4$ alkyl;

X is a direct bond or a straight or branched C$_1$–C$_4$ alkylene chain;

the symbol =Y represents

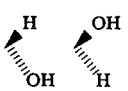

or =O;

Z is hydroxy, C$_1$–C$_6$ alkoxy or a group

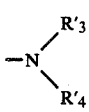

wherein each of R'$_3$ and R'$_4$ is, independently, hydrogen or C$_1$–C$_4$ alkyl;

the symbol ═══ represents a single or double bond, and the pharmaceutically acceptable salts thereof.

3. Compound of claim 2, wherein
R$_1$ is C$_1$–C$_4$ alkyl;
X is a direct bond or a straight or branched C$_1$–C$_4$ alkylene chain;
=Y is =O; and
Z is C$_1$–C$_6$ alkoxy or

wherein
each of R'$_3$ and R'$_4$ is independently hydrogen or C$_1$–C$_4$ alkyl.

4. Compound of claim 3, wherein
R' is methyl or ethyl;
X is —CH—(CH$_2$)$_2$—; and
Z is methoxy, ethoxy, —NH$_2$, —N(CH$_3$)$_2$ or —N(C$_2$H$_5$)$_2$.

5. Compound of claim 4, wherein
Z is methoxy, —N(CH$_3$)$_2$ or —N(C$_2$H$_5$)$_2$.

6. A compound selected from the group consisting of:
24-N,N-diethylcarbamoyl-4-methyl-4-azachol-5-en-3,12-dione;
24-N,N-diethylcarbamoyl-4-ethyl-4-azachol-5-en-3,12-dione;
24-N,N-dimethylcarbamoyl-4-dimethyl-4-azachol-5-en-3,12-dione;
24-N,N-dimethylcarbamoyl-4-ethyl-4-azachol-5-en-3,12-dione;
24-N,N-diethylcarbamoyl-4-methyl-4-azachol-5-en-12α-hydroxy-3-one;
24-N,N-diethylcarbamoyl-4-methyl-4-aza-5α-cholan-3,12-dione;
24-methoxycarbonyl-4-methyl-4-aza-chol-5-en-3,12-dione; and
24-methoxycarbonyl-4-methyl-4-aza-5α-cholan-3,12-dione.

7. A compound of formula (I) according to claim 1, wherein
R$_1$ is —OR$_2$, wherein R$_2$ is hydrogen, C$_1$–C$_4$ alkyl or a C$_2$–C$_{12}$ aliphatic or aromatic carboxylic acyl or a hydroxy protecting group X is a direct bond or a straight or branched C$_1$–C$_4$ alkylene chain;

the symbol =Y represents

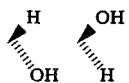

or =O;

Z is hydroxy or a group

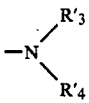

wherein each of R'$_3$ and R'$_4$ is, independently, hydrogen or C$_1$–C$_4$ alkyl; and the symbol ═══ represents a single or double bond, and the pharmaceutically acceptable salts thereof.

8. A 5α-reductase inhibiting pharmaceutical composition comprising an effective amount of a compound of formula (I) or a pharmaceutically acceptable salt thereof, according to claim 1, as the active substance, and a pharmaceutically acceptable carrier and/or diluent.

9. A method of inhibiting 5α-reductase in a patient in need of such inhibition, said method comprising administering to said patient an inhibiting amount of a compound of claim 1.

* * * * *